United States Patent
Uematsu et al.

(10) Patent No.: US 10,067,098 B2
(45) Date of Patent: Sep. 4, 2018

(54) ULTRASONIC FLAW DETECTION JIG, ULTRASONIC FLAW DETECTION METHOD AND METHOD OF MANUFACTURING ULTRASONIC FLAW DETECTION JIG

(71) Applicant: MITSUBISHI HEAVY INDUSTRIES, LTD., Tokyo (JP)

(72) Inventors: Mitsuyoshi Uematsu, Tokyo (JP); Yoshiharu Kuze, Tokyo (JP); Seiji Kobayashi, Tokyo (JP); Tomohiro Mizuno, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 367 days.

(21) Appl. No.: 14/763,166

(22) PCT Filed: Jan. 22, 2014

(86) PCT No.: PCT/JP2014/051189
§ 371 (c)(1),
(2) Date: Jul. 24, 2015

(87) PCT Pub. No.: WO2014/119436
PCT Pub. Date: Aug. 7, 2014

(65) Prior Publication Data
US 2015/0355146 A1    Dec. 10, 2015

(30) Foreign Application Priority Data
Feb. 1, 2013    (JP) .................................. 2013-018618

(51) Int. Cl.
*G01N 29/28*    (2006.01)
*G01N 29/22*    (2006.01)

(52) U.S. Cl.
CPC ............ *G01N 29/28* (2013.01); *G01N 29/221* (2013.01); *G01N 29/223* (2013.01); *G01N 2291/269* (2013.01); *G01N 2291/2636* (2013.01)

(58) Field of Classification Search
CPC .. G01N 29/043; G01N 29/221; G01N 29/223; G01N 29/24; G01N 29/28;
(Continued)

(56) References Cited

U.S. PATENT DOCUMENTS

2003/0021628 A1\* 1/2003 Gudaitis .................. F16B 5/01
403/408.1
2010/0198076 A1    8/2010 Kollgaard et al.
(Continued)

FOREIGN PATENT DOCUMENTS

CN    101694482 A    4/2010
DE    3633556 A1    4/1987
(Continued)

OTHER PUBLICATIONS

International Search Report dated Apr. 15, 2014, corresponding to International application No. PCT/JP2014/051189.
(Continued)

*Primary Examiner* — Manish S Shah
*Assistant Examiner* — Suman K Nath
(74) *Attorney, Agent, or Firm* — Kanesaka Berner and Partners LLP

(57)    ABSTRACT

An ultrasonic flaw detection jig includes a base section with which a probe of the ultrasonic inspection apparatus is brought into contact; and a prominence section provided for the base section and inserted into an inspection object hole of an inspection object. The inspection object hole includes a countersunk section connected with a main surface of the inspection object and extending from the main surface while
(Continued)

reducing a diameter; and a connection section connecting a bottom of the countersunk section and the rear surface of the inspection object. The prominence section has a conical shape corresponding to the shape of the countersunk section.

4 Claims, 7 Drawing Sheets

(58) Field of Classification Search
CPC ..... G01N 2291/0235; G01N 2291/044; G01N 2291/2636; G01N 2291/269; G10K 11/26; G10K 11/16
USPC .......................................... 73/644, 1.82, 617
See application file for complete search history.

(56) References Cited

U.S. PATENT DOCUMENTS

| 2012/0035862 A1 | 2/2012 | Kollgaard et al. |
| 2012/0174674 A1* | 7/2012 | Kollgaard ............ G01N 29/225 73/632 |

FOREIGN PATENT DOCUMENTS

| JP | 47-1117 Y | 1/1972 |
| JP | 54-81384 U | 6/1979 |
| JP | 58-92949 A | 6/1983 |
| JP | 63-126859 U | 8/1988 |
| JP | 5-4010 U | 1/1993 |
| JP | 5-40873 U | 6/1993 |
| JP | 9-133664 A | 5/1997 |
| WO | 2012/123724 A1 | 9/2012 |

OTHER PUBLICATIONS

International Preliminary Report on Patentability dated Aug. 13, 2015, corresponding to International Application No. PCT/JP2014/051189.
Office Action in JP Application No. 2013-018618, dated Jun. 7, 2017.
Extended European Search Report in EP Application No. 14746359.0, dated Aug. 26, 2016.

* cited by examiner

ULTRASONIC FLAW DETECTION JIG, ULTRASONIC FLAW DETECTION METHOD AND METHOD OF MANUFACTURING ULTRASONIC FLAW DETECTION JIG

RELATED APPLICATIONS

The present application is a National Phase of International Application Number PCT/JP2014/051189, filed Jan. 22, 2014, and claims priority of Japanese Patent Application No. 2013-018618 filed on Feb. 1, 2013.

TECHNIQUE FIELD

The present invention relates to an ultrasonic flaw detection jig, an ultrasonic flaw detection method and a method of manufacturing an ultrasonic flaw detection jig.

BACKGROUND ART

Regarding a non-destructive inspection technique, an ultrasonic inspection is known.

An ultrasonic inspection technique is disclosed in Patent Literature 1 (JP H09-133664A). Patent Literature 1 discloses covering an inspection surface of an inspection object with waveguide substance whose acoustic impedance value is equal to or approximate to that of the inspection object so that the inspection surface of the non-inspection object becomes flat. Also, Patent Literature 1 discloses that a waveguide is removed from the inspection object and attached to another inspection object (reference to para. 0021).

CITATION LIST

[Patent Literature 1] JP H09-133664A

SUMMARY OF THE INVENTION

By the way, a countersink is sometimes provided for a structure. FIG. 1 is a sectional view schematically showing a structure 2 in which a countersink 1 is formed. As shown in FIG. 1, the structure 2 includes a main surface 5 and a rear surface 6. The countersink 1 is formed to pass through the structure 2 between the main surface 5 and the rear surface 6. The countersink 1 has a countersunk section 3 and a connection section 4. The countersunk section 3 is connected with the main surface 5 at its one end and extends from the main surface 5 toward the rear surface 6 while reducing the diameter. The connection section 4 connects the bottom of the countersunk section 3 and the rear surface 6. The diameter of the connection section 4 is constant.

When the countersink 1 is formed in the structure 2, a flaw is sometimes formed on the wall of the countersunk section 3 and the connection section 4. Therefore, after the countersink 1 is formed, the countersink 1 is inspected.

The inventors of the present invention are considering use of the ultrasonic inspection, to inspect whether a flaw exists in the countersunk section 3 and the connection section 4. When the ultrasonic inspection is carried out, the countersink 1 is buried with a waveguide material (ultrasonic flaw detection jig) to lead the ultrasonic into the wall of the countersunk section 3. After that, the ultrasonic is emitted to the structure through the waveguide material and the wall of the countersunk section 3 from the probe to determine whether the existence or non-existence of the flaw is determine based on the reflected wave.

Many countersinks 1 are sometimes formed in the structure 2. In such a case, there would be a case to apply the waveguide material which has been applied to one countersink 1, to another countersink 1, to be described in Patent Literature 1. However, the hole diameter would be different among the countersinks 1, due to a manufacturing error. Also, the hole diameter is different for reasons in case of design. When the hole diameter is different, the waveguide material does not fit with the other countersink 1. Thus, the waveguide material has to be prepared for every countersink 1 so that great labor is spent to inspect all the countersinks 1.

Therefore, an object of the present invention is to provide an ultrasonic flaw detection jig, by which inspection can be made easily even when the hole diameter is different.

The ultrasonic flaw detection jig according to the present invention includes a base section with which a probe of an ultrasonic inspection apparatus is brought into contact; and a prominence section provided for the base section and inserted into an inspection object hole of an inspection object. The inspection object hole has a countersunk section connected with a main surface of the inspection object and extending from the main surface while reducing a diameter, and a connection section which connects the bottom of the countersunk section and a rear surface of the inspection object. The prominence section has a conical shape corresponding to the shape of the countersunk section.

An ultrasonic flaw detection method according to the present invention includes arranging an ultrasonic flaw detection jig on a main surface of an inspection object having an inspection object hole; and inspecting an inspection object hole by bringing a probe of an ultrasonic inspection apparatus into contact with an ultrasonic flaw detection jig after the arranging. The ultrasonic flaw detection jig includes a base section and a prominence section provided for the base section and inserted into the inspection object hole. The inspection object hole has a countersunk section connected with the main surface at its one end, and extending from the main surface while reducing a diameter, and a connection section connecting a bottom of the countersunk section and a rear surface of the inspection object. The prominence section has a conical shape corresponding to the shape of the countersunk section. The arranging includes arranging the ultrasonic flaw detection jig so that the prominence section is inserted into the inspection object hole.

An ultrasonic flaw detection jig which is manufactured by a manufacturing method according to the present invention includes a base section with which a probe of an ultrasonic inspection apparatus is brought into contact; and a prominence section provided for the base section and inserted into an inspection object hole of the inspection object. The inspection object hole has a countersunk section connected with a main surface of the inspection object at its one end and extending from the main surface while reducing a diameter, and a connection section connecting a bottom of the countersunk section and a rear surface of the inspection object. The prominence section has a conical shape corresponding to the shape of the countersunk section. The method of manufacturing the ultrasonic flaw detection jig includes supplying a resin material to a mold of a mold member; hardening the supplied resin material; removing the hardened resin material from the mold; and shaping the removed resin material to obtain the ultrasonic flaw detection jig.

According to the present invention, the ultrasonic flaw detection jig can be provided, by which the inspection can be made easily even when the hole diameter is different.

DESCRIPTION OF EMBODIMENTS

Hereinafter, an ultrasonic flaw detection jig according to embodiments of the present invention will be described with reference to the attached drawings.

Figure 1:
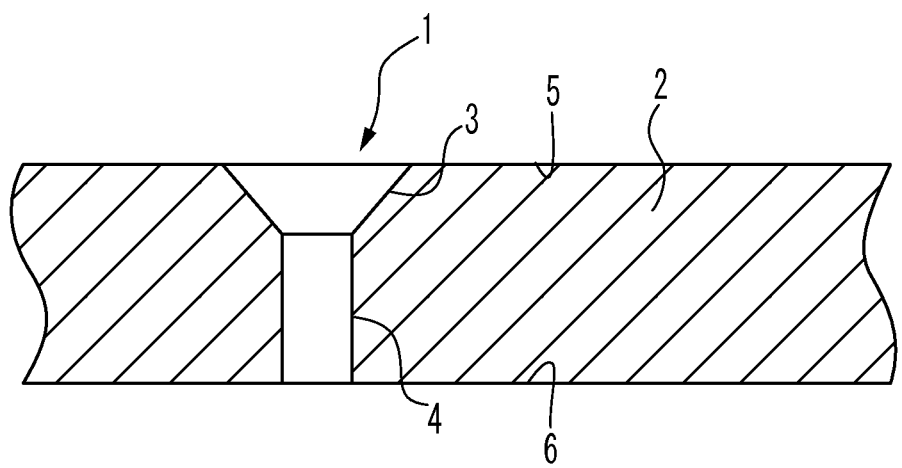
FIG. 1 is a sectional view schematically showing a structure in which a countersink is provided.

First, an inspection object will be described. The ultrasonic flaw detection jig according to the present embodiment is used to inspect a countersink 1 (an inspection object hole) provided for a structure 2 (an inspection object) as shown in FIG. 1. That is, the countersink 1 passes through the structure 2 between the main surface 5 and the back surface 6 and has a countersunk section 3 and a connection section 4. Note that the section shape of the countersink 1 in the plane which is parallel to the main surface 5 is circular.

In the present embodiment, the structure 2 is assumed to be a composite material (fiber-reinforced composite material) which is used for the fuselage of an aircraft. Also, the countersink 1 is assumed to be a hole for a fastener to be inserted.

Figure 2:
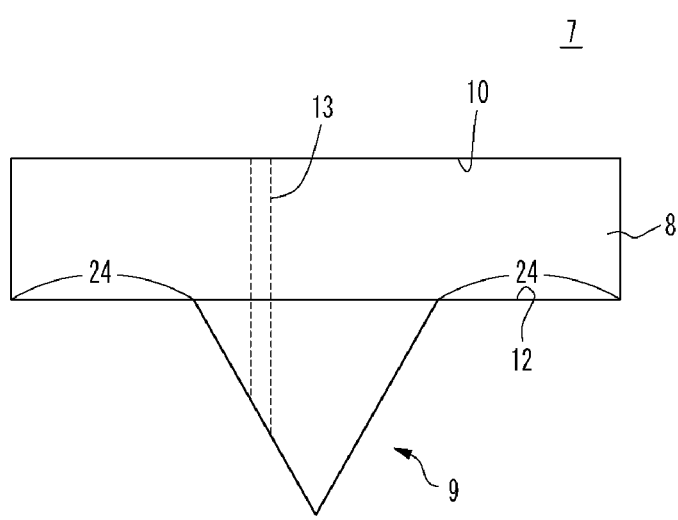
FIG. 2 is a sectional view showing an ultrasonic flaw detection jig.

Next, the ultrasonic flaw detection jig 7 will be described. FIG. 2 is a sectional view showing an ultrasonic flaw detection jig 7.

As shown in FIG. 2, the ultrasonic flaw detection jig 7 has a base section 8 and a prominence section 9.

The base section 8 has a first surface 10 and a second surface 12. The first surface 10 is a surface with which a probe is brought into contact. The second surface 12 is an opposite surface to the first surface 10 and is a surface which is contact with the main surface 5 of the structure 2.

The prominence section 9 is provided for the base section 8 to protrude from the second surface 12. The prominence section 9 is a portion to be inserted in the countersink 1 in an inspection. The prominence section 9 has a conical shape in correspondence to the countersunk section 3.

Also, the base section 8 includes a flange region 24 disposed to surround the prominence section 9. The flange region 24 is brought into contact with the main surface 5 of the structure 2 in the inspection.

Moreover, a contact medium supplying hole 13 is provided for the base section 8. The contact medium supplying hole 13 is provided to supply the contact medium to an interface between the prominence section 9 and the wall of the countersunk section 3. The contact medium supplying hole 13 is provided to pass through the base section 8. One end of the contact medium supplying hole 13 is connected with the first surface 10 and the other end thereof is connected with the surface of the prominence section 9.

When the structure 2 is a composite material, for example, a resin material and so on are used as the material of the base section 8 and the prominence section 9, and an epoxy resin, a polyester resin and so on are desirably used.

Figure 3:
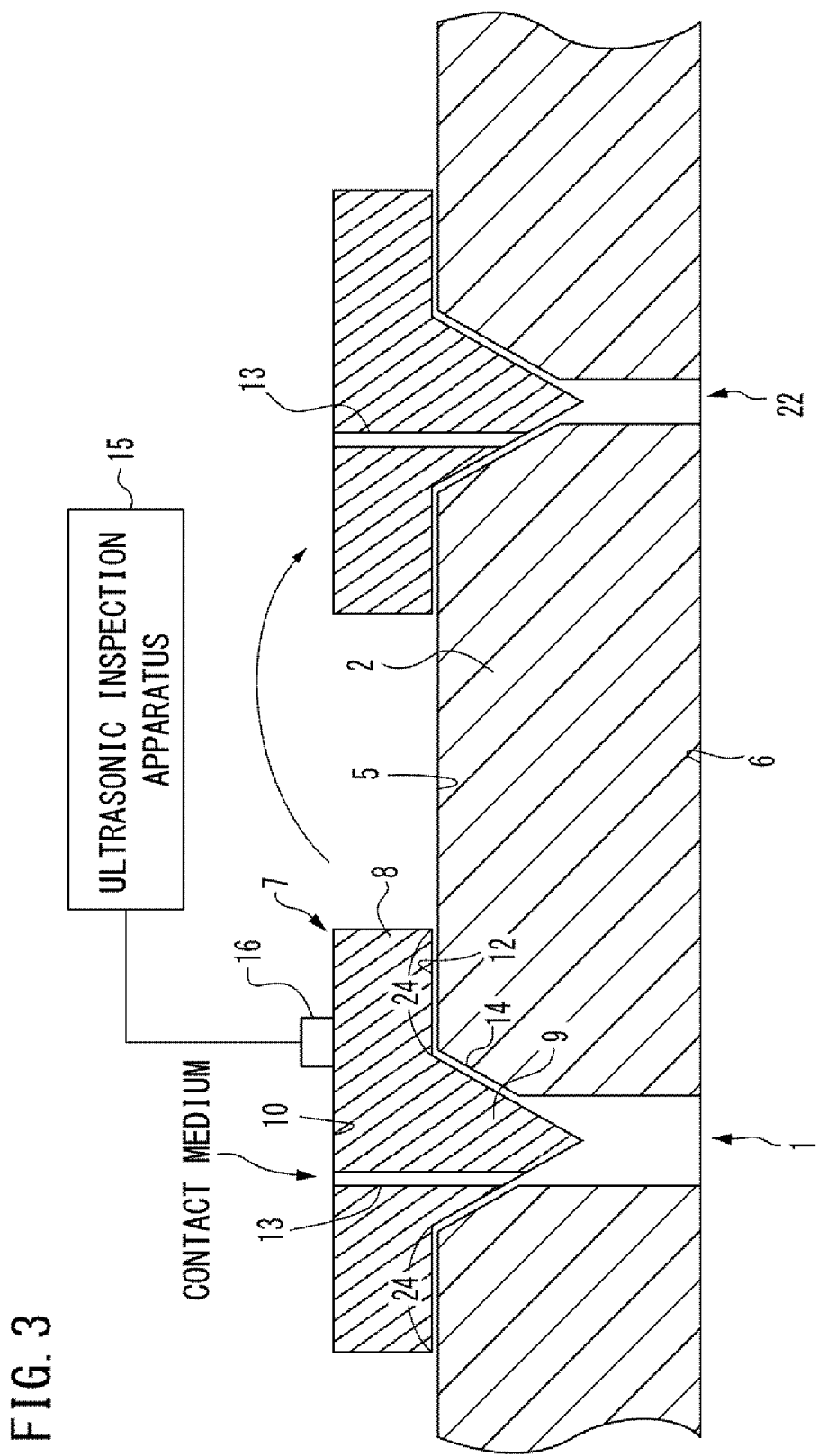
FIG. 3 is a diagram schematically showing an ultrasonic flaw detection method.

Next, an ultrasonic flaw detection method will be described. FIG. 3 is a diagram schematically showing the ultrasonic flaw detection method.

First, the ultrasonic flaw detection jig 7 is arranged on the main surface 5 of the structure 2. At this time, the ultrasonic flaw detection jig 7 is arranged for the prominence section 9 to be inserted in the countersink 1. Here, the prominence section 9 has a conical shape and corresponds to the shape of the countersunk section 3. Therefore, the wall 14 of the countersunk section 3 is covered with the prominence section 9. Also, the base section 8 is brought into contact with the main surface 5 in the flange region 24.

Next, the contact medium (e.g. water) is supplied to the interface between the prominence section 9 and wall 14 through the contact medium supplying hole 13. For example, the contact medium is supplied to the contact medium supplying hole 13 from an injector (not shown).

Moreover, the probe 16 of an ultrasonic inspection apparatus 15 is brought into contact with the first surface 10. Ultrasonic wave is emitted to and hit against the wall 14 through the ultrasonic flaw detection jig 7 from the probe 16. The ultrasonic inspection apparatus 15 detects the reflected wave from the wall 14 by the probe 16, and determines the existence or non-existence of a flaw of the wall 14 based on the detection result. That is, the wall 14 is inspected and the countersink 1 is inspected by the ultrasonic inspection.

After the inspection ends, the ultrasonic flaw detection jig 7 is removed from the countersink 1, and the removed ultrasonic flaw detection jig 7 is installed in another countersink 22. Thus, the ultrasonic flaw detection is carried out for the other countersink 22, like the countersink 1.

Here, there is a case that the size (a hole diameter) of the other countersink 22 is different from that of the countersink 1 due to a manufacturing error and a reason in case of the design. When the prominence section 9 corresponds to the whole shape of the countersink 1, there is a case that the prominence section 9 does not conform to the other countersink 22. However, in the present embodiment, the prominence section 9 does not have the shape corresponding to the whole countersink 1 and has a conical shape. If the wall inclination of the countersunk section 3 is the same between the countersink 1 and the other countersink 22, the prominence section 9 fits to the wall of the other countersink 22. It is not necessary to prepare the ultrasonic flaw detection jig 7 for every countersink. Even when a plurality of countersinks with different hole diameters exist, it is possible to inspect them by using the ultrasonic flaw detection jig 7.

Also, in the present embodiment, the contact medium supplying hole 13 is provided in the ultrasonic flaw detection jig 7. For example, the main surface 5 sometimes is a ceiling surface. In such a case, when the contact medium with a high fluidity (e.g. water) is merely supplied to the wall 14 of the countersunk section 3, the contact medium flows out immediately. A medium must be adopted so as to adhere to the wall 14 as the contact medium to prevent the medium from flowing out. When the contact medium adhering to the wall 14 is used, the wall 14 must be washed after the inspection. There is a case that it is not possible to wash the wall 14, depending on a kind of the structure 2 and the application of the countersink 1. On the other hand, in the present embodiment, because the contact medium is supplied through the contact medium supplying hole 13, the contact medium can be stably supplied to the wall 14 of the countersunk section 3 even if a medium (e.g. water) flowing out immediately is used as the contact medium. Because the water and so on can be used as the contact medium, it is not necessary to wash the structure 2 after the inspection.

Moreover, according to the present embodiment, the flange region 24 is provided. Because the flange region 24 is provided, a worker can treat the ultrasonic flaw detection jig 7 by having the flange region 24. That is, the handling can be improved. In addition, in the flange region 24, the base section 8 functions as a delay material. Therefore, it is possible to make it easier to inspect.

Next, an example of a method of manufacturing the ultrasonic flaw detection jig 7 according to the present embodiment will be described. FIG. 4A to FIG. 4D are diagrams schematically showing a method of manufacturing the ultrasonic flaw detection jig 7.

Figure 4A:
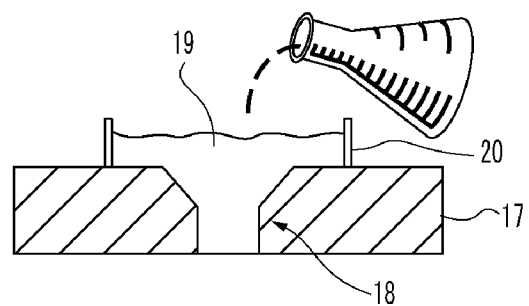
FIG. 4A is a diagram schematically showing a method of manufacturing the ultrasonic flaw detection jig.

First, as shown in FIG. 4A, a mold member 17 is prepared. A countersink 18 has been formed in the mold member 17 to have a shape corresponding to a countersink as an inspection object. A side wall member 20 is arranged on the mold member 17 to surround the countersink 18. A mold is configured from the countersink 18 and the side wall member 20. A mold releasing agent (e.g. petrolatum) (not shown) is applied onto the mold side walls (side walls of the countersink 18 and the side wall member 20). After that, a resin material 19 is supplied into the mold. As the resin material 19, a material of a heat hardening type is used.

Figure 4B:
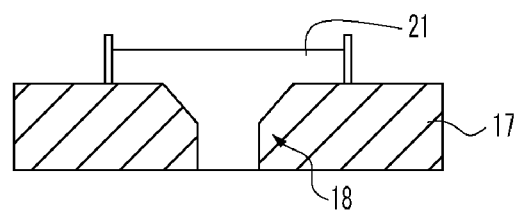
FIG. 4B is a diagram schematically showing the method of manufacturing the ultrasonic flaw detection jig.

Next, as shown in FIG. 4B, the resin material 19 is hardened. Specifically, the mold member 17 is set in a heating apparatus (oven and so on) and is heated. The resin material 19 is hardened through the heating.

Figure 4C:
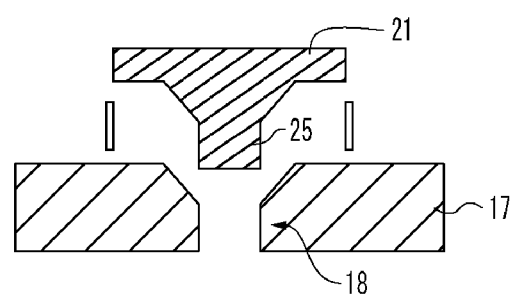
FIG. 4C is a diagram schematically showing the method of manufacturing the ultrasonic flaw detection jig.

Next, the hardened resin material 21 is removed from the mold member 17, as shown in FIG. 4C. The resin material 21 has a tip section 25 of the shape corresponding to the countersink 18.

Figure 4D:
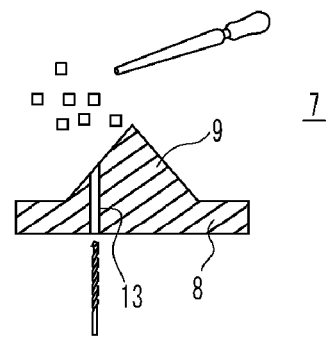
FIG. 4D is a diagram schematically showing the method of manufacturing the ultrasonic flaw detection jig.

Next, as shown in FIG. 4D, the resin material 21 is processed. Specifically, the tip section 25 is processed to have a conical shape by using a file and so on, and the prominence section 9 is completed. Also, the contact medium supplying hole 13 is formed by using a drill and so on.

In the above, the ultrasonic flaw detection jig 7 is obtained.

Next, by comparing the present embodiment with a comparison example, the operation effect of the present embodiment will be described. FIG. 5A to FIG. 5E are diagrams schematically showing the ultrasonic flaw detection method according to the comparison example.

Figure 5A:
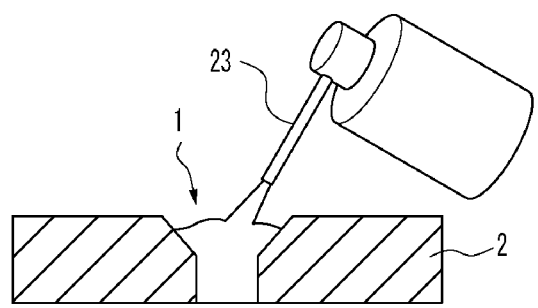
FIG. 5A is a diagram schematically showing the ultrasonic flaw detection method according to a comparison example.

As shown in FIG. 5A, in the comparison example, the resin material 23 is directly injected into the countersink 1 (the inspection object hole) provided for the structure 2 as the inspection object.

Figure 5B:
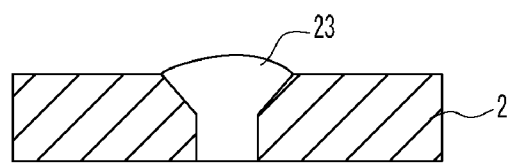
FIG. 5B is a diagram schematically showing the ultrasonic flaw detection method according to the comparison example.

Next, the injected resin material 23 is hardened, as shown in FIG. 5B. At this time, if the structure 2 is of a large-size, the structure 2 cannot be arranged in the heating apparatus such as the oven. Therefore, the injected resin material 23 is hardened at the normal temperature.

Figure 5C:
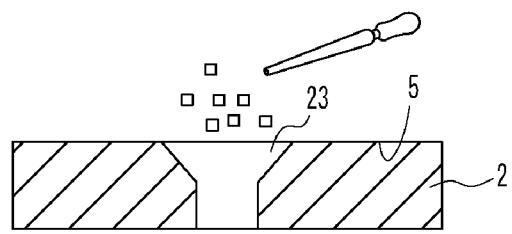
FIG. 5C is a diagram schematically showing the ultrasonic flaw detection method according to the comparison example.

Next, the resin material 23 is processed such that the main surface 5 becomes flat, as shown in FIG. 5C.

Figure 5D:
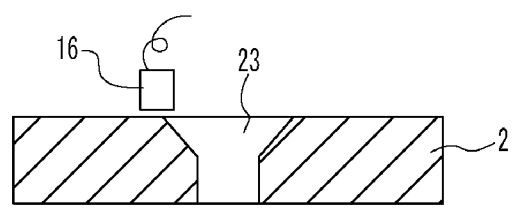
FIG. 5D is a diagram schematically showing the ultrasonic flaw detection method according to the comparison example.

Next, as shown in FIG. 5D, the probe 16 is brought into contact with the surface of the resin material 23 to carry out an inspection by the ultrasonic inspection.

Figure 5E:
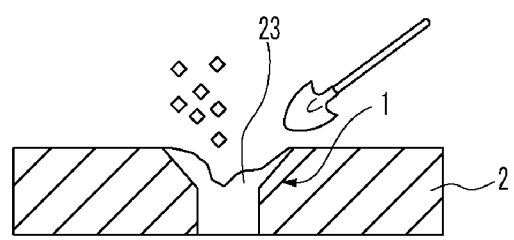
FIG. 5E is a diagram schematically showing the ultrasonic flaw detection method according to the comparison example.

After the inspection, as shown in FIG. 5E, the resin material 23 is scraped off from the countersink 1. The resin material 23 cannot be applied to another countersink because it is scraped off.

Compared with the above-mentioned comparison example, in the present embodiment, the mold member 17 is used upon the manufacturing. The mold member 17 can be made smaller in size than the structure 2, and can be made small to a degree that it can be arranged in the heating apparatus. Therefore, in case of the hardening, the resin material 19 can be heated. As a result, the resin material 19 can be hardened in a short time. For example, when the resin material is used which is hardened by leaving for 8 hours at the normal temperature, it becomes possible to harden by heating for 30 minutes to 1 hour at 60° C.

Also, in the comparison example, the resin material 23 is directly injected into the countersink 1 as the inspection object. Therefore, it is difficult to carry out the mold release processing beforehand. This is because there is a case that the applied mold releasing material cannot be removed from the countersink 1 when the mold releasing material (petrolatum and so on) is applied. On the other hand, in the present embodiment, because the mold member 17 is used, the mold release processing can be easily carried out. Therefore, the ultrasonic flaw detection jig 7 can be removed from the mold member 17.

In the present embodiment, because the mold release processing can be carried out, the ultrasonic flaw detection jig 7 can be removed from the countersink 1. That is, unlike the comparison example, it is not necessary to scrape off the resin material 19. Therefore, the ultrasonic flaw detection jig 7 can be applied to another countersink 22. That is, the present embodiment is more favorable from the point that it is possible to reuse, compared with the comparison example.

Note that in the embodiment, a case that the inspection object is the composite material which is used for the fuselage of the aircraft has been described. Also, a case that the inspection object hole is a hole for the fastener insertion has been described. However, the inspection object and the inspection object hole are not limited to them and the present invention can be applied to another use if the inspection object hole has the countersunk section 3 and the connection section 4.

The present application is based on Japanese Patent Application No. JP 2013-018618 and claims a priority based on it. The disclosure thereof is incorporated herein by reference.

The invention claimed is:

1. An ultrasonic flaw detection jig configured to inspect an inspection object hole formed in an inspection object having a main surface and a back surface, the inspection object hole comprising a conical recess extending from the main surface of the inspection object toward an inside of the inspection object, and a connection hole section connecting a bottom part of the conical recess and the back surface of the inspection object, the ultrasonic flaw detection jig comprising:

a base section having a main surface and a back surface, a probe of an ultrasonic inspection apparatus being disposed to contact the main surface of the base section; and a prominence section provided to protrude from the back surface of the base section to have a conical shape coming into contact with the conical recess; and a contact medium supply hole disposed to pass straightly through the jig from a position separated by a predetermined distance from the probe on the main surface of the base section to a contact surface of the prominence section with the conical recess to allow the contact medium to be supplied from the main surface of the base section to a surface of the conical recess, when the jig is attached to the inspection object hole.

2. The ultrasonic flaw detection jig according to claim 1, further comprising:

a flange region disposed for the base section to contact the main surface of the inspection object and to surround the prominence section.

3. An ultrasonic flaw detection method for inspecting an inspection object hole formed in an inspection object having a main surface and a back surface, the inspection object hole comprising a conical recess extending from the main surface of the inspection object toward an inside of the inspection object, and a connection hole section connecting a bottom part of the conical recess and the back surface of the inspection object, the method comprising:

arranging an ultrasonic flaw detection jig on a main surface of an inspection object having an inspection object hole;

inspecting the inspection object hole by bringing a probe of an ultrasonic inspection apparatus into contact with the ultrasonic flaw detection jig, after the arranging, wherein the ultrasonic flaw detection jig comprises:

a base section having a main surface and a back surface;

a prominence section provided to protrude from the back surface of the base section to have a conical shape coming into contact with the conical recess; and a contact medium supply hole disposed to pass straightly through the jig from a position separated by a predetermined distance from the probe on the main surface of the base section to a contact surface of the prominence section with the conical recess, wherein the arranging comprises:

arranging the ultrasonic flaw detection jig such that the prominence section is inserted in the inspection object hole, wherein the inspecting comprises:

attaching a probe of an ultrasonic inspection apparatus to come into contact with the main surface of the base section;

supplying contact medium to a contact surface of the prominence section with the conical recess from the main surface of the base section through the contact medium supply hole; and inspecting the inspection object hole by using the probe.

4. The ultrasonic flaw detection method according to claim 3, wherein the inspection object is a fiber reinforced composite material.

* * * * *